United States Patent [19]

Rabischong et al.

[11] 3,993,056
[45] Nov. 23, 1976

[54] ORTHOPAEDIC APPLIANCES

[75] Inventors: Pierre Rabischong, Saussan; Jean Pierre Louis Bel, Montpellier, both of France

[73] Assignee: Institut National de la Sante et de la Recherche Medicale, Paris, France

[22] Filed: Jan. 21, 1976

[21] Appl. No.: 651,033

[52] U.S. Cl. .................. 128/89 R; 128/DIG. 20; 128/80 G
[51] Int. Cl.² ......................................... A61F 5/04
[58] Field of Search ............... 128/89 R, 87 R, 83, 128/80 R, 80 F, 80 G, DIG. 20, 78, 25; 3/1.1, 1.2

[56] References Cited
UNITED STATES PATENTS

| | | | |
|---|---|---|---|
| 891,181 | 6/1908 | Mitchell | 128/DIG. 20 |
| 2,522,853 | 9/1950 | Black | 128/80 F |
| 3,868,952 | 3/1975 | Hatton | 128/78 |
| 3,923,045 | 12/1975 | Talati et al. | 128/25 R |

*Primary Examiner*—John D. Yasko
*Attorney, Agent, or Firm*—Brooks Haidt Haffner & Delahunty

[57] ABSTRACT

An orthopaedic appliance which enables paralytics to stand erect has a fabric garment formed in separate pieces to be tightly wrapped around body parts located between joints the pieces having an inflatable support structures in the form of vertical tubes and devices connecting garment pieces located on opposite sides of a body joint in the form of a separate row of rigid parallel pins attached to the inflatable structure each garment piece and a pivot which can be hydraulically or otherwise driven, interconnecting the rows of pins. The inflatable tubes are located in elongate fabric sheaths and the pins are inserted in fabric sheaths defined between the tube sheaths so that when the tubes are inflated they clamp the pins between them.

17 Claims, 13 Drawing Figures

ORTHOPAEDIC APPLIANCES

This invention relates to orthopaedic appliances for enabling paralytics to stand erect.

Orthopaedic appliances are known which consist of a single garment of inextensible fabric, adjusted to the lower limbs and to a portion of the trunk of a person and furnished with inflatable tubes or profiles attached vertically to the outside of the garment in order to confer upon the garment a rigidity sufficient to support part of the weight of the body whilst relieving the muscles and the skeleton of the person so that paralytics wearing such a garment can stand erect and move about.

These appliances known as ortheses enable paraplegics and victims of accidents to stand up sooner during periods of functional reeducation.

The known orthesis must, however, be deflated every time the paralytic wearing it wants to move from the upright to the seated position and reinflated upon return to the upright position, which necessitates permanent availability of a source of compressed gas.

In addition these one-piece ortheses are not easily fitted to the patients and must be made to measure for each of them.

In accordance with the present invention there is provided an orthopaedic appliance for enabling paralytics to stand erect, comprising a flexible garment of inextensible fabric formed of a plurality of separate garment pieces each positionable on and adjustable to envelop tightly a body portion located between two joints of a paralysed person, an inflatable structure including a plurality of parallel, flexible and inflatable tubes attached to each garment piece to extend substantially vertically over the portion of the garment piece which encloses the outer side of the body part, in use of the appliance, each pair of adjacent garment pieces which are located on opposite sides of a body joint, in use of the appliance being connected together by a mechanical support device having two rows of rigid pins for attachment to respective garment pieces and connected together by a mechanical articulation arranged to be located at the level of the said body joint and means for attaching each row of pins to the inflatable structure of the respective garment piece.

A orthopaedic appliances of this construction can enable paralytics to stand erect and to move from the upright position to the seated position and vice versa without having to employ a source of compressed gas. It can also be motorized in order to facilitate walking.

The orthopaedic appliance can facilitate assembly by fitters, of an appliance fitted to the measurements of a patient by employing a modular assembly of parts each of which is selected from a limited number of corresponding elements of different sizes. This can also simplify repairs reducing the time of non-availability of an appliance and immobilization of the paralytic since it only requires the damaged module to be replaced by another standard module.

The mechanical articulations transmit the vertical forces from one piece of garment to the other and facilitate moving from the upright position to the seated position and vice versa without having to deflate and reinflate the tubes. Each articulation may be furnished with an articular latch which locks it in the extended position while standing erect. It may likewise include a hydraulic or electric motor which facilitates movements, such as walking.

The mechanical support devices comprise two rows of attachment pins and the inflatable structures attached to the sides of the pieces of garment includes flexible sheaths open at least one of their ends, into each of which at least one of the pins engages these flexible sheaths being directly interposed between two inflatable tubes or between two sheaths each containing an inflatable tube so that the pins are pinched by the tubes when the latter are inflated, to ensure a secure attachment of the pins to the pieces of the garment, which is sufficient to transmit the vertical forces due to the weight of the paralytic.

The attachment of the pins to the garment pieces by pushing them into and clamping them with the inflatable tubes is particularly simple, making the device easy to assemble and to dismantle without any tools. It can also enable a certain lateral displacement of the pins in the sheaths which facilitates confirming the appliance to the morphology of the body of the patient and avoids the risk of the pins exerting painful pressures locally.

Some embodiments of the invention are described below by way of example with reference to the accompanying drawings in which:

FIG. 8 is a perspective of the garment, shown without the inflatable structures;

Figure 1:
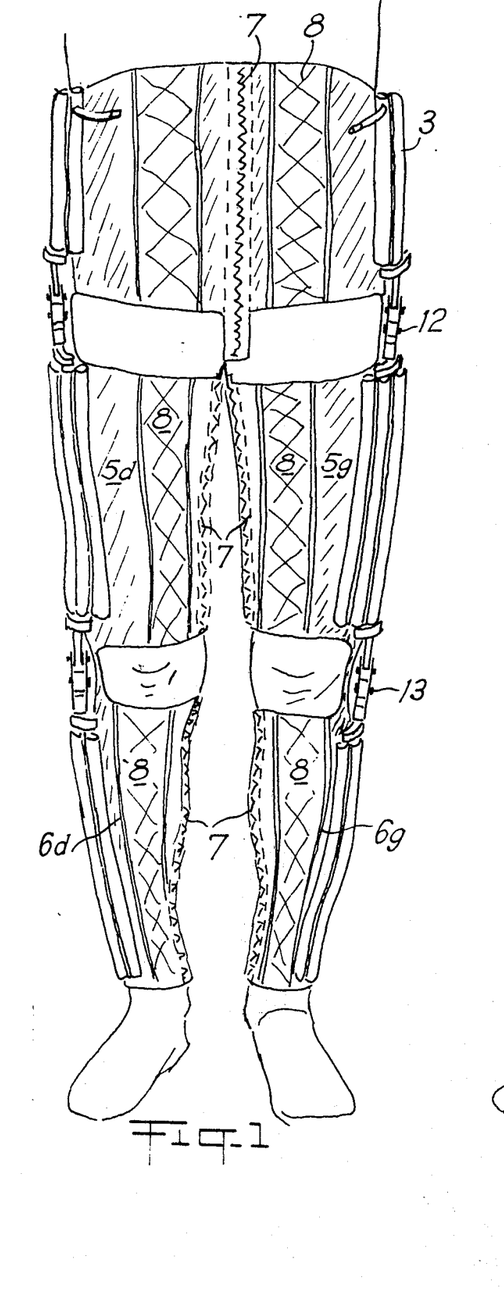
FIGS. 1 and 2 are front and profile views respectively of an orthopaedic appliance in accordance with the invention.
Figure 2:
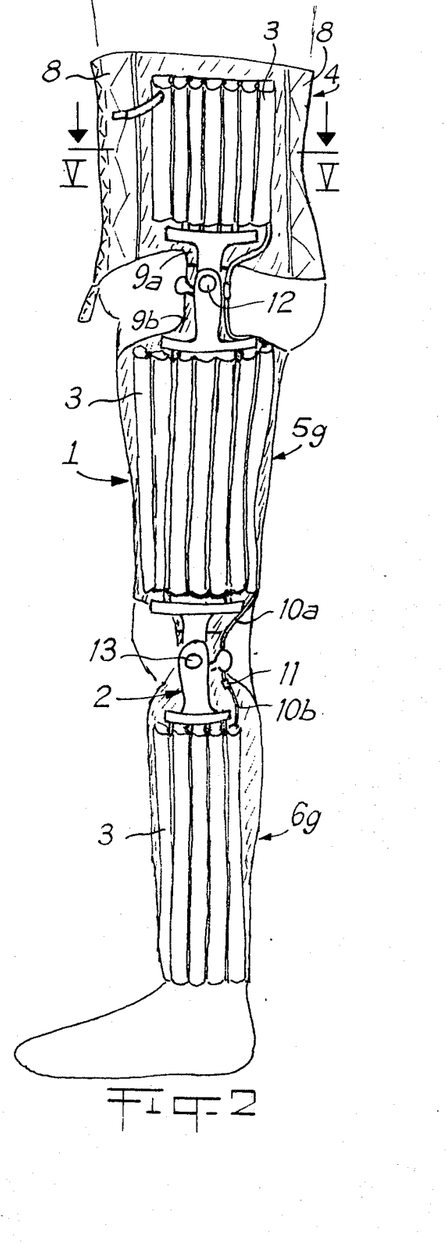

FIGS. 1 and 2 represent a patient paralysed in the lower limbs, wearing an orthopaedic appliance in accordance with the invention, composed on the one hand of a garment 1 and on the other hand of articulated mechanical devices 2.

The garment is of the type known as an orthesis, that is to say, a garment of fabric inextensible in warp and weft, covering the lower limbs and all or a portion of the trunk and serving as a support for inflatable profiled structures.

These inflatable structures are flexible longitudinal tubes 3 which, once inflated, confer stiffness to the garment and transmit loads vertically, thus relieving the limbs and the skeleton.

The garment 1 is composed of a number of pieces or modules each enveloping one portion of the body located between two joints whilst leaving these joints free.

The garment shown comprises first of all a bodice 4 enveloping a portion of the trunk, and which may vary with the origin and type of paralysis for example paraplegia D12, paraplegia D4, Lobstein's disease etc., The garment also includes two thigh pieces 5d and 5g enveloping the thighs and two calf-pieces 6d and 6g enveloping the calves. The modules 5d and 5g as well as 6d and 6g are symmetrical.

The pieces of garment are produced, for example, from very strong polyamide fabric or ventilated cotton fabric. They include in known manner means enabling them to be closed after they have been wrapped round the corresponding portion of the body, for example, zip-fasteners 7 or any other equivalent closure means (laces, buttons, hooks and eyes, etc..) these closure means enable the garment to be laid out flat and the user to lie down on the garment in order to put it on. Each piece of the garment likewise includes means enabling it to be carefully adjusted to the corresponding portion of the body, for example, laces 8 or any other equivalent means.

In a variant shown in FIG. 8 the slide fasteners 7 and the system of adjustment by laces 8 are replaced by a closure of Velcro type. Each piece of garment 4, 5d, 5g, 6d, 6g consists simply of a band of fabric bearing inflatable tubes, which is wrapped round a portion of the body located between two joints. Each of these bands bears at its two ends located opposite one another, a male and a female facing only one of which, 7a, can be seen in the drawing, composed of fibres forming loops which interpenetrate one another and get entangled. A closure of this kind facilitates adjustment of the garment to the measurements of the patient and constitutes at the same time an attachment device easy to use by handicapped persons.

Each garment module or piece is produced in a certain number of sizes, for example, 12 sizes for a range of children and adults, the differences between sizes depending on the height and development. Each piece of garment has lateral assembly flaps 9 (FIG. 2) such as 9a, 9b, located facing one another, which are furnished at their free ends with means enabling them to be attached to one another, these means being, for example, press-studs, buckles, laces or any other equivalent means.

Once the various modules are attached to one another they constitute a garment adjusted to the patients body.

Onto each of these flaps 9 is fixed a small flexible pipe 10, such as pipes 10a, 10b which communicates by one end with the inflatable tubes 3 incorporated into the same piece of garment. The other end of this pipe is equipped with a connector 11 enabling the two tubes fixed to two facing flaps to be connected together.

These tubes enable continuity of the pneumatic circuit to be ensured and all the tubes 3 to be inflated from a single valve or a number of smaller valves.

The two mechanical devices 2 located on each side of the appliance comprise mechanical articulations 12, 13 located at the level of the hip and knee joints. These articulations (FIG. 3) called articular latches enable the various positions to be ensured. They consist, for example, of a head in the form of a fork 12a, 13a connected to a top part and bearing a pivot 12b, 13b about which pivots an arm 12c, 13c integral with a bottom part.

Figure 3:
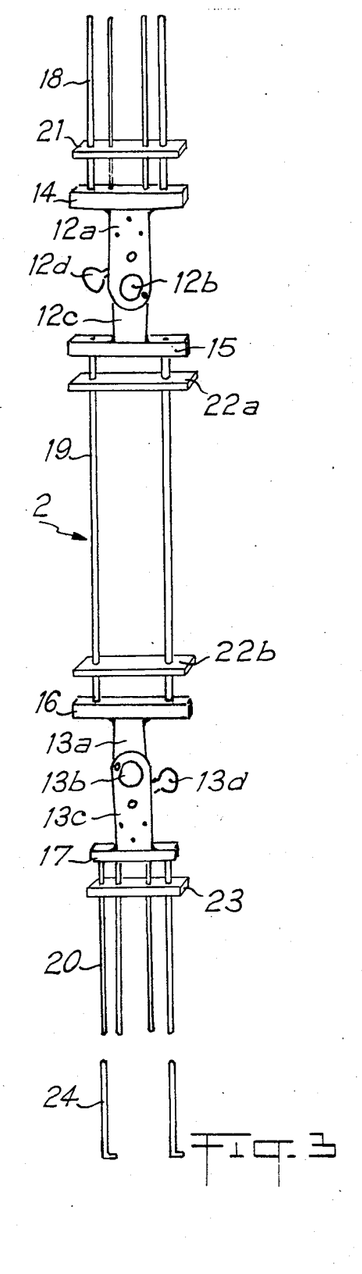
FIGS. 3 and 4 are front views of two mechanical support devices including passive or active articulations.

On opposite sides of each articulation the device 2 includes a curved plate 14, 15, 16, 17 for attachment of pins. These plates 14, 15, 16, 17 bear against the garment 1 on opposite sides of the articulation above or below the inflatable tubes.

The mechanical device 2 includes rigid pins or rods which enable it to be integrated with the garment 1.

Figures 4, 7:
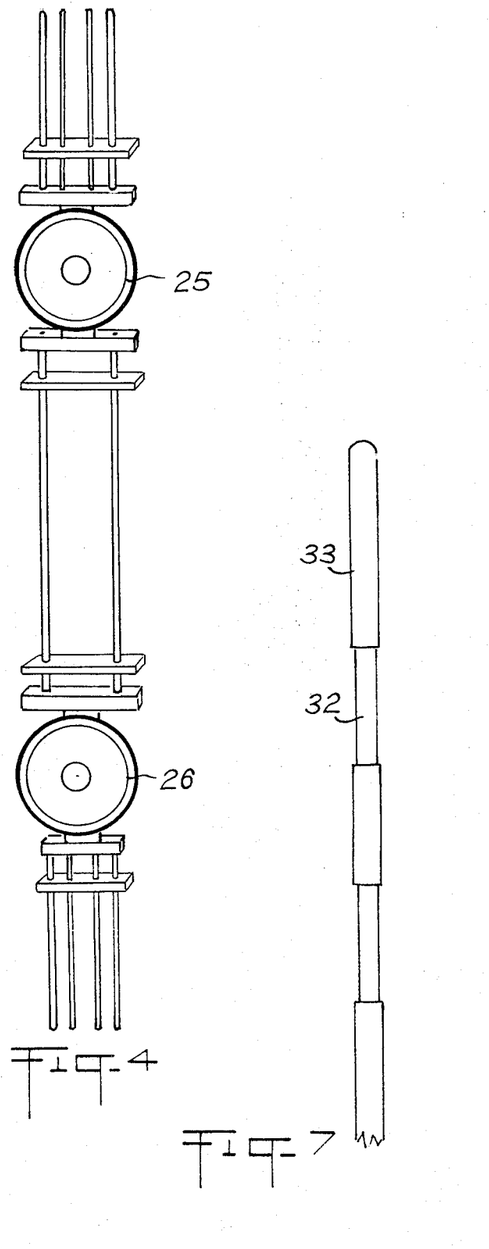
FIG. 7 shows a pin in elevation.
Figure 4:
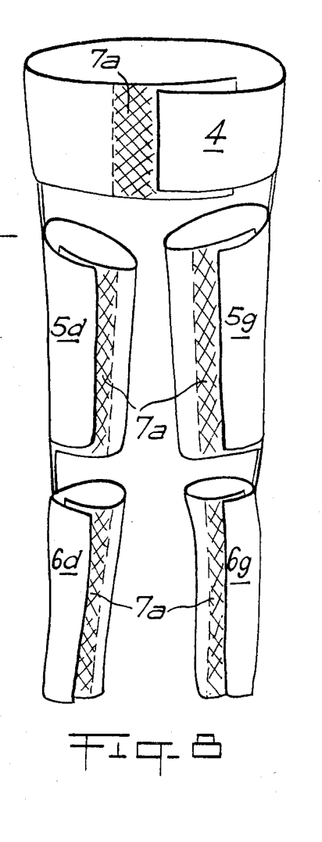

The devices illustrated in FIGS. 3 and 4 have, for example, four pins 18 for attachment to the bodice 4, two pins 19 for attachment onto a thigh piece 5d or 5g and four pins 20 for attachment onto a calf piece 6d or 6g. The number of pins is given simply by way of example and may vary. The bottom ends of the pins 18 are attached to the plate 14 by any known means, for example, the ends of the pins can be threaded and screwed into the plates. Similarly the top ends of the pins 19 are attached to the plate 15 and the bottom ends to the plate 16. As a variant the pins 19 may be in two portions attached one to the plate 15 and the other to the plate 6, if necessary overlapping, which enables the contour of the thigh to be followed and facilitates adjustment of the articulations for height. The top ends of the pins 20 are attached to the plate 17.

The mechanical device 2 may optionally include collars for adjustment of height and through which the pins pass. As shown it includes one adjusting collar 21 on the hip, two adjusting collars 22a and 22b on the thigh piece and one adjusting collar 23 at the top of the calf piece. These collars are locked by any means, for example, by means of screws, at an adjustable level.

FIG. 3 shows in its lower part a variant embodiment in which two of the pins 20 have an extension downwards 24 which bears against the footwear. This variant is intended for patients whose skeletons cannot support the load from standing vertically, these rods enabling the skeleton to be relieved of the weight of the body.

FIG. 4 shows a modified mechanical device in which the passive articulations 12 and 13 are replaced by motorized articular activators 25 and 26 of any known type, electric, hydraulic or pneumatic.

The source of energy and the electronic operating and control circuits are carried by the patient. The orthesis then becomes an active orthesis enabling walking step by step stabilized by two walking sticks.

The mechanical articulations 12 and 13 include a locking mechanism 12d, 13d which enables them to be locked in various positions especially those which correspond with the vertical position and the seated position.

Figure 5:
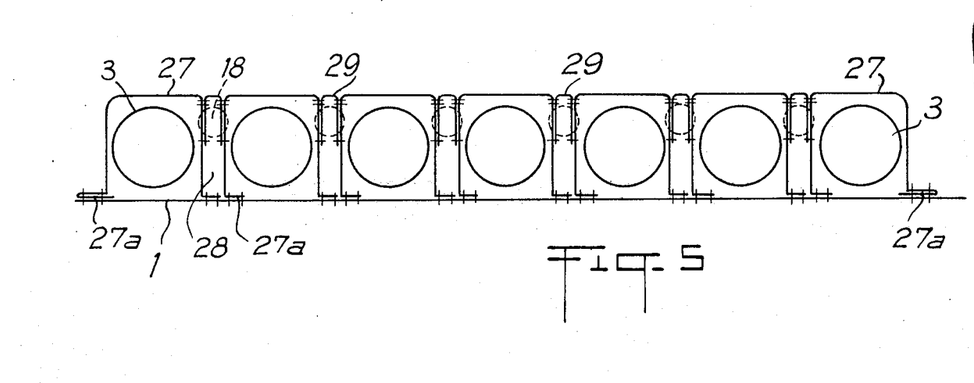
FIGS. 5 and 6 are sections taken along the line V—V in FIG. 2 showing two forms of inflatable structure and methods of attachment of the pins of the mechanical support devices.

FIG. 5 shows a part section passing through the line V—V in FIG. 2, on which appears the original method of attachment of the mechanical device 2 onto the pieces of garment 1.

In this Figure is seen the garment 1 bearing the inflatable tubes 3 which are arranged in known manner inside cells placed side by side, formed by envelopes 27 folded back on themselves and stitched to the garment 1 at their two ends by stitches 27a.

The pins 18, 19, 20 engage in secondary sheaths 28 interposed between the inflatable tubes and open at their two ends, so that when the tubes are inflated the pins are pinched laterally by the pressure and held locked to the garment 1. As can be seen in FIG. 5 the sheaths 28 are bounded by the walls of two adjacent cells which are spaced apart a few millimeters and which are connected together at the end opposite from the garment by a tape 29 stitched to the two walls so that the sheaths 28 occupy the whole of the gap lying between two adjacent cells.

Figure 6:
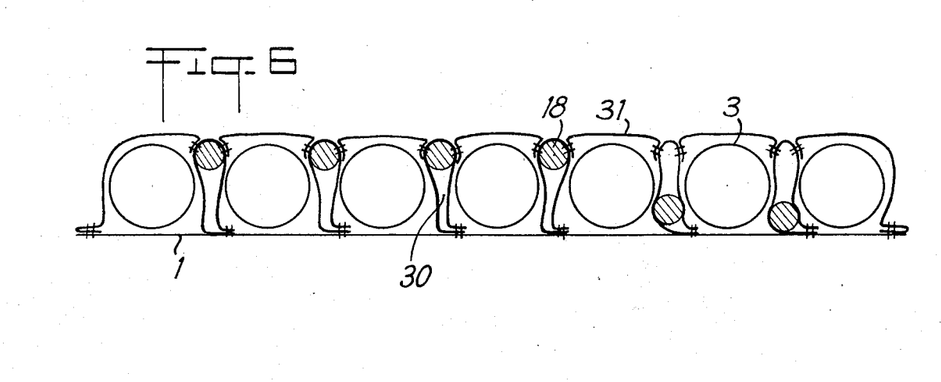

FIG. 6 shows a variant including secondary sheaths 30 in which engage the pins 18, which are formed by folded fabric onto which are stitched strips 31 which compose an envelope surrounding both the sheaths 31 and the inflatable tubes 3.

It can be seen that the attachment of the pins onto the garment enables the height of pins engaged in the sheaths 28 or 30 to be easily varied when the inflatable tubes are deflated, which enables the height of the mechanical articulations 12 and 13 to be adjusted, so that they are located exactly at the level of the joints.

This method of attachment offers the advantage that transmission of forces between the garment and the mechanical devices is distributed over the whole length of the pins which avoids the body of the patients being subjected to high pressures localised at certain points.

FIG. 7 represents a preferred form of pin consisting of a succession of sections 32 having a reduced outer diameter alternating with sections 33 of larger diameter. This form improves the adhesion between the pins and sheaths in which they engage and consequently the transmission of the vertical forces.

Static tests in tension have been carried out in order to measure the stripping force of one pin. This varies between 13daN and 43daN when the pressure varies between 1 bar and 3 bars for a pin having an outer diameter of 6mm and a length of 150 mm threaded into a sheath having a diameter of 55 mm.

These values show that the forces transmitted are sufficient for supporting the weight of a man with a pressure of the order of 1.5 bars. Greater forces may be obtained by increasing the pressure or the diameter of the pins.

Figure 9:
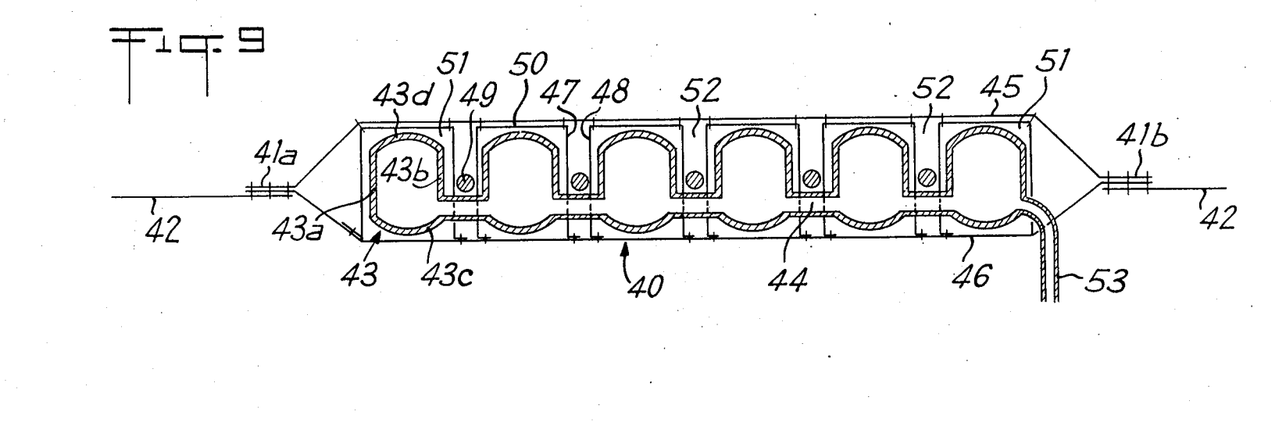
FIGS. 9 and 10 are similar sections to those of FIGS. 5 and 6 showing an alternative form of inflatable structure in the deflated and inflated state respectively.
Figure 10:
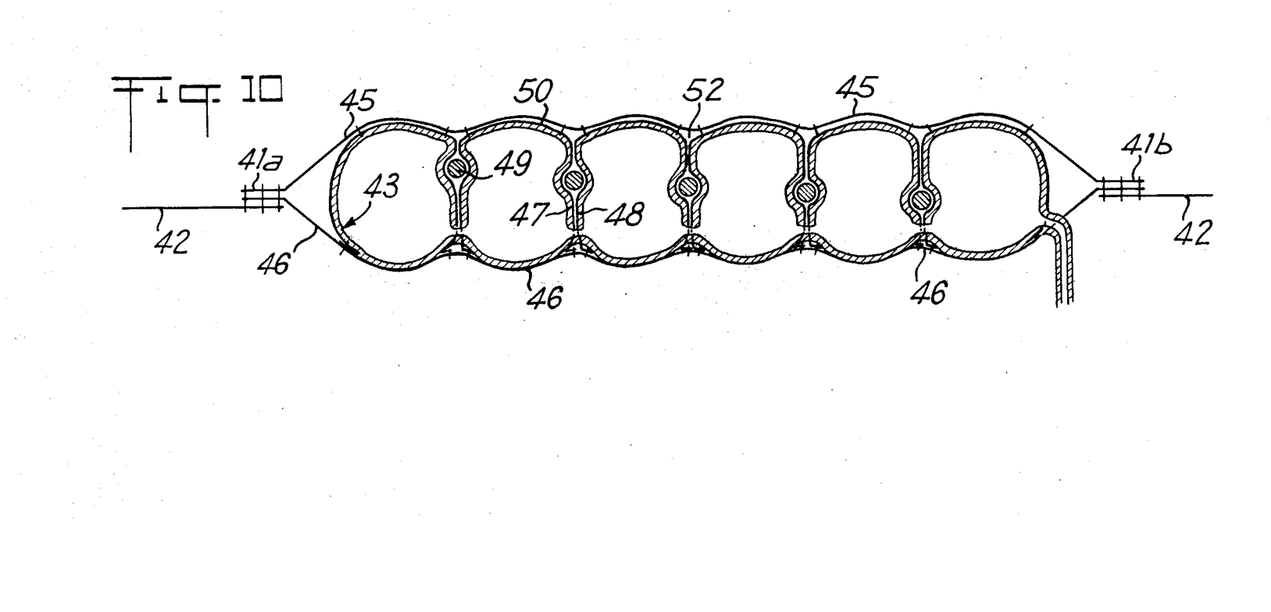

FIGS. 9 and 10 show a transverse section through an inflatable structure 40 attached vertically onto the side portions of each of the pieces of a garment 42 of an orthesis.

The structure shown in FIGS. 9 and 10 is attached to the garment by stitches 41a and 41b which connect its edges to those of a window cut out of the garment 42.

The structure shown in FIGS. 9 and 10 has, for example, six inflatable and deformable tubes 43, for example, tubes of neoprene or any other elastomer.

In the deflated state these tubes exhibit two flat sidefaces 43a and 43b which are placed perpendicular to the surface of the garment 42 and are joined together by two curved surfaces 43c and 43d. This form of the section of the tubes ensures better power of deformation of the structure. The tubes 43 are connected together by a pipe 44.

The tubes 43 are put inside an envelope formed on two bands of fabric 45 and 46. Inside this envelope the tubes 43 are separated from one another by pairs of transverse partitions of fabric 47 and 48.

These transverse partitions are stitched at their two ends of the bands 45 and 46 forming the envelope. The partitions of one and the same pair are separated from one another by a gap or a few millimeters in which engages a pin 49 used for attachment of the mechanical articulations.

Preferably the partition 47 placed on one side of a tube and the partition 48 placed on the other side of the same tube are connected together by a strip 50 with which they form one and the same piece which constitutes, once it has been stitched to the bands 45 and 46, an inflatable sheath 51 containing an inflatable tube 43.

Between two sheaths 51 is interposed a secondary sheath 52, called the fitting sheath in which is housed a pin 49.

The fittings sheaths are open at least one of their two ends in order to enable fitting in the pin 49. When the tubes 43 are inflated they deform as shown in FIG. 10, bringing about deformation of the sheaths 51 which pinch the pins 49 laterally so that they become integral with the structure.

A pipe 53 enables all the tubes 43 to be inflated simultaneously.

It will be observed in FIG. 10 that the pins 49 may not be aligned. Actually the volume of the fitting sheaths 52 enable the pins 49 to shift perpendicular to the structure at the time of putting it under pressure in order to adapt to the contour and morphology of the limbs.

Figure 11:
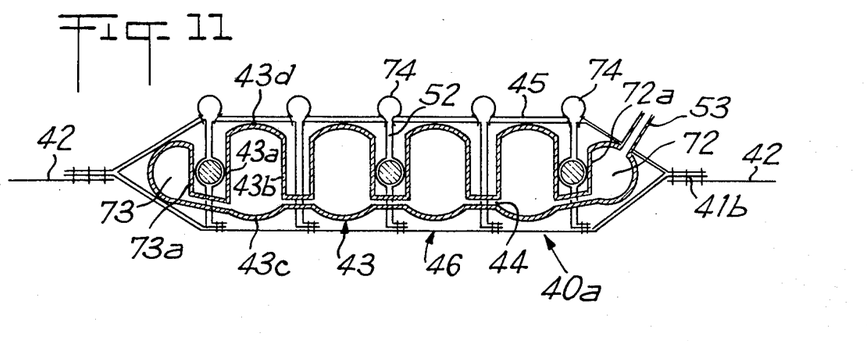
FIG. 11 is a transverse section similar to that of FIG. 5 showing another alternative form of inflatable structure in the deflated state.

FIG. 11 shows a transverse section through a variant upon the inflatable structures 40a, similar to the structure 40 as FIG. 9 in the uninflated state. The parts similar to those as FIG. 9 are shown with the same reference numbers.

The inflatable tubes 43 which compose the central portion of the structure 40a are identical with those of the structure 40.

On the other hand the structure 40a has at each end two tubes 72 and 73 of smaller section having only one flat sideface 72a and 73a located on the structure side.

The envelope put round the tubes is formed of two bands of fabric, 45 on the outside and 46 on the inside.

The outer band 45 has undulations 74 located opposite the fitting-sheaths 52, which form bellows. These undulations enable elongation of the outer band 45 and facilitate the enveloping deformation of the pneumatic structure which enables it to adopt easily to the morphology of the limbs without squeezing the latter when the tubes 43 are inflated.

Figure 12:
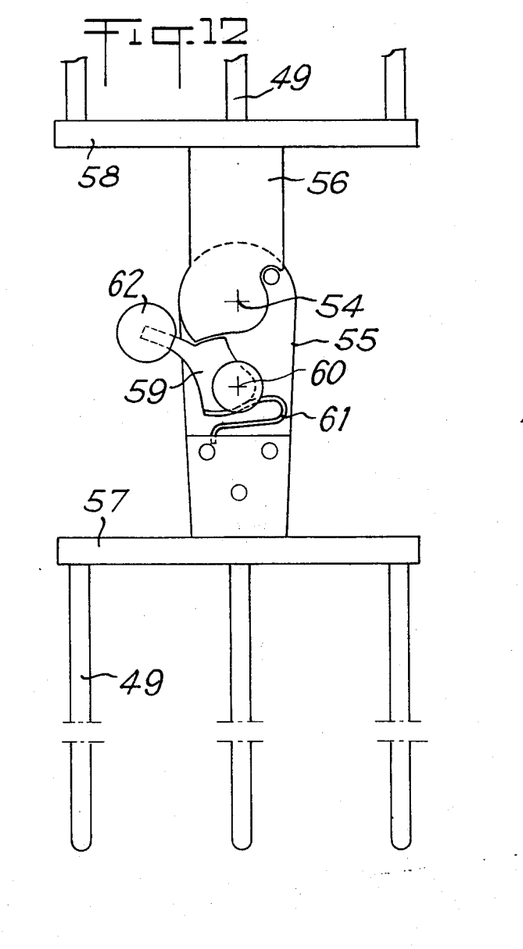
FIG. 12 is an elevation of part of a mechanical support device including an articular latch and FIG. 13 is a vertical section through part of a motorized articulation.

FIG. 12 shows a front view of a mechanical articulation including a latch for locking, called an articular latch.

This latch is composed of two elements articulated with respect to one another about a pivot 54 and is placed at the height of a joint, for example, the knee. Each of the two elements has attachment pins 49 which are fitted into fitting sheaths 52 in a pneumatic structure attached to the garment, for example, a structure as in FIGS. 9 and 10.

The lower element is composed of a head 55 in the form of a fork only one side of which is shown for clarity in the drawing. The upper element consists of an arm 55 which fits between the two sides of the head 55 and pivots about the pivot 54. Each of the two elements 55 and 56 is attached to a curved plate 57, and 58 respectively, bearing the pins 49. Locking of the articular latch in the straight position is ensured by means of an arm 59 which pivots about a pivot 60 carried by the head 55 and which forms a stop for the end of the arm 56. A spring blade 61 keeps the arm 59 in the locked position and a knob 62 enables the latch to be unlocked by exerting on the arm 59 a torque opposed to that of the spring 61. As a variant, unlocking may be obtained by means of a remote controlled electromagnet.

Figure 13:
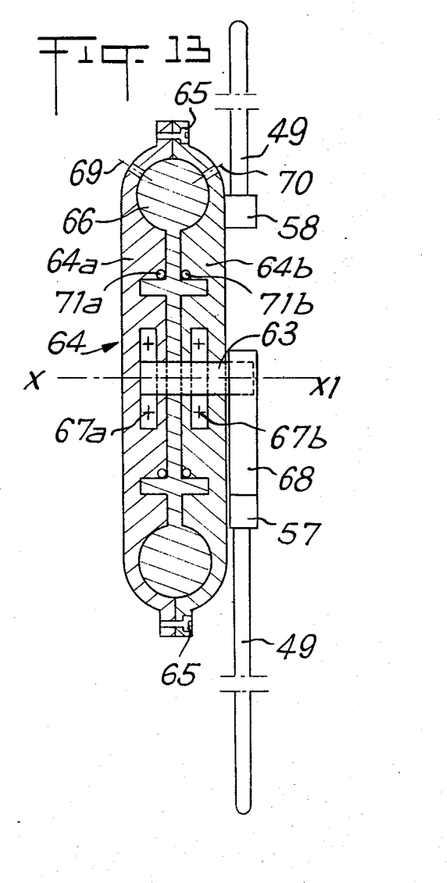

FIG. 13 shows a transverse section of a motorised articulation. In this Figure are found again the attachment pins 49 and the curved plates 57 and 58 located on opposite sides of the articulation.

The axis of articulation is the axis $X-X_1$ which is the axis of a shaft 63.

The motor is a hydraulic motor composed of a stator in two parts 64a and 64b assembled together by screws 65. This stator is integral with the pin carrier plate 58. Inside the stator 64 is mounted a one-piece rotor 66 integral with the shaft 63 which is mounted in two ballbearings. 67a and 67b. An arm 68 integral with the curved plate 57 is fixed to the shaft 63.

Feed is effected through an inlet orifice 69 and exhaust through an outlet orifice 70. The motor enables a rotation of the rotor with respect to the stator of 120° to be obtained. Rotation when out of pressure is facilitated by two ballbearings 71a and 71b. The hydraulic motor may be replaced by an electric motor equipped with a reducing gear.

We claim:

1. An orthopaedic appliance for enabling paralytics to stand erect, comprising of a flexible garment of inextensible fabric, formed of a plurality of separate garment pieces each positionable on and adjustable to envelop tightly a body portion located between two joints of a paralysed person and each garment piece having an outer portion which in use of the appliance encloses the outer side of the body part, an inflatable structure on each garment piece and including a plurality of parallel, flexible and inflatable tubes attached to said garment piece to extend substantially vertically over the said outer portion thereof, pairs of adjacent ones of said garment pieces being located on opposite sides of a body joint, in use of the appliance, a mechanical support device connecting together the garment pieces of each said pair of adjacent pieces said devide comprising two rows of rigid pins and a mechanical articulation interconnecting said rows of pins and arranged to be located at the level of the said body joint, and means for attaching each said row of pins to said inflatable structure of a respective one of said pair of adjacent garment pieces located on opposite sides of the said joint.

2. An appliance as claimed in claim 1, wherein each of said garment pieces and said pins is selected from a group consisting of a limited number of said pieces or pins respectively all of different sizes.

3. An appliance as claimed in claim 1, wherein each said pin attachment comprises longitudinal flexible sheaths on said inflatable structure, the sheaths having opposed ends and each being interposed between two of said inflatable tubes of said inflatable structure, the said sheaths being open at at least one of their said opposed ends, and having at least one of the said pins inserted therein, whereby said pins are pinched by said tubes when the latter are inflated.

4. An appliance as claimed in claim 3, wherein each said mechancial support device comprises two arms each having first and second ends, the said connected together at their said first ends by said mechanical articulation, and two curved plates respectively attached each to the said second ends of said arms and carrying one of said rows of pins, said pins of each of said two rows of rigid pins being cylindrical and of small diameter, and pins of each row being parallel with one another, each said pin having opposite ends and being attached by one of its said ends to said curved plate and having a portion of its length inserted in one of said flexible sheaths.

5. An appliance as claimed in claim 1, wherein said garments pieces of each said pair of adjacent garment pieces have opposed tabs with means for connecting said tabs to one another.

6. An appliance as claimed in claim 5, wherein each said tab carries a small flexible pipe having opposite ends and which communicates by one said end with said tubes of said inflatable structure attached to said garment piece to which said tab is attached and is equipped at the other said end with a connector for connection to the connector of said tube carried by said tab of the other said garment piece of said pair of pieces.

7. An appliance as claimed in claim 3, wherein each said inflatable structure consists of a series of elongated parallel cells each containing a respective one of said inflatable tubes, each cell being formed by a flexible envelope having inner and outer walls.

8. An appliance as claimed in claim 7, wherein each said envelope is formed by a piece of fabric having opposite ends, said piece of fabric being stitched at its said ends to the outside of said garment piece adjacent envelopes in said series being separated by a gap, a strip of fabric being stitched to said adjacent envelopes to close said gap and form a sheath having opposite end, said sheath being open at at least one of said ends, and having one of said pins inserted therein.

9. An appliance as claimed in claim 3, wherein the said tubes of each said inflatable structure are deformable, interconnected and parallel with one another and each of said tubes has in the deflated state thereof a transverse cross-section exhibiting two opposed, flat parallel sidewalls.

10. An appliance as claimed in claim 9, wherein each said garment piece has a window cut out of said outer portion thereof, an envelope of fabric having inner and outer walls is stitched over the whole of its periphery to the edges of said window in said garment piece and said tubes of said inflatable structure of said garment piece are located inside said envelope.

11. An appliance as claimed in claim 10, wherein for each said tube of said inflatable structure, a strip of fabric having opposite ends is stitched at its two said ends to one of said walls of said envelope and is stitched to the other of said walls of said envelope at at least two points to form a deformable sheath receiving said tube, said two points being spaced apart by a distance which is substantially equal to the distance separating said two flat sidewalls of said tube received in said sheath, and gaps being defined between adjacent deformable sheaths forming auxiliary sheaths such said auxiliary sheath being bounded by two adjacent deformable sheaths and said inner and outer walls of said envelope, having opposite ends with at least one of said ends open, and receiving one of said pins for transverse movement in said sheath.

12. An appliance as claimed in claim 10 wherein said outer wall of said envelope has vertical undulations which form a deformable bellows to allow the structure to conform to the shape of the body part enveloped by said garment piece.

13. An appliance as claimed in claim 1 wherein each of said pins has a plurality of longitudinal sections of reduced diameter alternating with sections of larger diameter.

14. An appliance as claimed in claim 1, wherein each of said garment pieces consists of a piece of fabric having opposed ends and closure means of Velcro type is provided on said opposite ends of the piece of fabric, whereby the said piece of fabric can be wrapped around a body part to tightly envelop the body part and the ends joined together by said closure means to retain the piece of fabric tight on the body part.

15. An appliance as claimed in claim 4 wherein said articulation of said mechanical support is motorized.

16. An appliance as claimed in claim 15, wherein said articulation is motorised by an hydraulic motor having a stator integral with one of said curved plates and a rotor integral with the other of said curved plates.

17. An appliance as claimed in claim 10, wherein said inflatable structure includes two lateral tubes having a smaller cross-section than said vertical extending tubes.

* * * * *

UNITED STATES PATENT OFFICE
CERTIFICATE OF CORRECTION

PATENT NO. : 3,993,056
DATED : November 23, 1976
INVENTOR(S) : Pierre Rabischong and Jean-Pierre Louis Bel It is certified that error appears in the above-identified patent and that said Letters Patent are hereby corrected as shown below:

Identifier [30] Foreign Application Priority Data:

January 24, 1975 France.......75/02.281 has been omitted

Col. 5, line 15 - "patients" should read --patient--

Col. 7, line 31 - "devide" should read --device--
(Claim 1)

Signed and Sealed this

Fifteenth Day of February 1977

[SEAL]

Attest:

RUTH C. MASON
Attesting Officer

C. MARSHALL DANN
Commissioner of Patents and Trademarks